United States Patent [19]

Fournier

[11] Patent Number: 5,363,198
[45] Date of Patent: Nov. 8, 1994

[54] APPARATUS AND METHOD FOR MEASURING SMOKE OPACITY OF A PLUME OF SMOKE USING AN ARRAY OF LIGHT BEAMS

[76] Inventor: Thomas J. Fournier, 2140 Stephen Ter., Ann Arbor, Mich. 48103

[21] Appl. No.: 973,617

[22] Filed: Nov. 9, 1992

[51] Int. Cl.$^5$ ............................................. G01N 15/06
[52] U.S. Cl. ..................................... 356/438; 356/437
[58] Field of Search ....................... 356/437, 438, 439; 250/221, 222, 575

[56] References Cited

U.S. PATENT DOCUMENTS 4,448,534  5/1984  Wertz et al. ........................ 356/436
4,719,360  1/1988  Kontani et al. ..................... 356/438

*Primary Examiner*—Richard A. Rosenberger
*Assistant Examiner*—Robert Kim
*Attorney, Agent, or Firm*—Harness, Dickey & Pierce

[57] ABSTRACT

A two dimensional light beam array from which a plume of smoke, such as from a diesel engine, passes. Beams of light are projected across the array by light sources for detection by light detectors in order to measure the transmittance or opacity of the beam of smoke between any given source and detector. By projecting beams of light in two dimensions across the array, the diameter and length of intersection of the light beam which projects through the diameter may be determined. To determine this length enables a calculation of a smoke density value for that plume of smoke. Also, by projecting beams of light in two dimensions across the array the position of the smoke plume within the array may be determined.

16 Claims, 3 Drawing Sheets

APPARATUS AND METHOD FOR MEASURING SMOKE OPACITY OF A PLUME OF SMOKE USING AN ARRAY OF LIGHT BEAMS

BACKGROUND OF THE INVENTION

Diesel engines typically emit plumes of smoke which inherently contain particulate matter. Measurement of diesel smoke opacity is of importance to a variety of fields including environmentalists, diesel engine manufacturers, service technicians and diesel owners. One method of evaluating diesel smoke uses a beam of light is directed through an exhaust plume, which is partially absorbed, depending upon the density and size of the particles. The amount of light which is blocked while attempting to pass through the plume is a measure of the opacity of the exhaust plume.

Smoke opacity can be used as an indication of proper engine function as well as engine pollution output. The Federal Environmental Protection Agency (EPA) uses diesel smoke opacity measurements during the type approval of engine systems, and some states and municipalities require periodic smoke opacity testing of diesel powered vehicles. Accordingly, it is desirous to have a continuous, real-time measurement system for determining the opacity of a plume of smoke as it exits an exhaust pipe. Furthermore, the smoke opacity is closely related to another measurement of particulate matter within the smoke plume, the smoke density. As some emission test programs require measurement of the smoke density, it becomes important to be able to calculate the smoke density of a plume of smoke in a relatively straight-forward manner. Smoke opacity is related to smoke density according to the following equation as defined by the Beer-Lambert Law:

$$T = e^{(-KL)}$$

Where:
T=Transmittance (%), where $T=(1-N/100)$,
N=Opacity (%)
e=Base of Natural Logarithm
K=Extinction Coefficient (Smoke Density)
L=Light Path Length
Therefore:

$$K = -\frac{LN(T)}{L}$$

It can be seen from the above equations that the values necessary to determine the smoke density of a plume of smoke are the transmittance, which is a measure of the amount of light which passes through the plume of smoke, and L, the length of intersection between the exhaust plume and the light beam. Also, additional calculations yield both the particle size and the particle density of the particles contained in the exhaust plume.

Current end of line diesel smoke opacity meters may be divided into two broad categories, each of which has particular limitations. The first such system is a full flow measurement system. The typical full flow system consists of a single beam of light which traverses the smoke plume while passing from a light source to a light detector. The source and detector are located a fixed distance apart, affixed to a rigid hoop or horseshoe bracket which allows the diesel smoke to pass undisturbed between the optical devices. There are several major drawbacks of such a system. First, placement of the device at the center of the smoke plume is critical to accurate test results, yet no means exists to automatically check for accurate placement. Therefore, it is possible that high smoke opacity values will go undetected because of inaccurate placement. For example, if the device is not aligned so that the light beam is directed across a diameter of the smoke plume, the opacity value will be reduced. In such a system, it is difficult to detect whether or not the optical beam is directed across a diameter of the plume. A second drawback of the full flow system is that because the length between the source and detector is fixed while the length across the plume varies in accordance with exhaust pipe diameter, a measured opacity value taken with the full flow system can not be immediately converted into smoke density units. The length of the light path that intersects the smoke must be known in order to determine the smoke density. In order to determine the intersection length, the operator must measure the diameter of the exhaust pipe, then align the source and detector so as to project light beams through that measured diameter.

A second system for measuring the opacity of a plume of smoke is a partial flow measurement system. Exhaust smoke is forced down a probe and hose assembly by engine exhaust pressure or by a separate pump. The smoke then passes through a sampling tube and is swept away by clean air at the ends of the tube. Because the tube is of a fixed length, the opacity measurement of the light passing through the tube is immediately usable for determining the smoke density; however, there remains several disadvantages to such a system. A partial flow measurement system requires a probe, a hose assembly, and possibly a separate pump. This system is more costly, has a slower time response, increases the amount of sample mixing during transport of the smoke through the apparatus, requires much maintenance as particulate matter tends to clog the apparatus, is much larger, is subject to sample condensation when used in cold weather, and is fairly awkward to implement on tall exhaust stacks (e.g., on a diesel truck).

SUMMARY OF THE INVENTION

This invention is directed towards an improved system for measuring the smoke opacity and density of a plume of smoke. A two-dimensional light array is placed where the smoke plume exits an exhaust pipe so that the plume passes through the array. The two-dimensional array enables the determination of the position of maximum opacity through the plume and also enables the determination of the length of intersection of the beam of light at the maximum opacity point. The system further determines if the array is properly placed in relation to the plume and generates an error signal when the array is not properly aligned. There are several advantages to this system. First, it is a full flow system and therefore does not suffer from disadvantages associated with partial flow systems. However, unlike prior full flow systems, the operator need not measure the diameter of the exhaust pipe, when seeking the smoke density, as the light array will determine the diameter at the point of maximum opacity through the exhaust plume. Also, because the diameter of the plume is determined by the array, the array may be used to determine the smoke opacity and the smoke density of plumes of varying sizes, as an array larger than a majority of exhaust pipes could be designed.

This system is implemented by placing a two-dimensional light array above an exhaust pipe or stack where the plume exits the exhaust pipe or stack. The two-dimensional array contains a series of matched light source and light detector pairs with the source located transversely across from the detector, and the light detector detects light emitted by its corresponding source. Matched source-detector pairs are placed along both dimensions so that substantially perpendicular light beams are projected across the array. The number of source-detector pairs depends upon the desired resolution, as a greater resolution requires a greater number of source-detector pairs per unit length.

The source-detector pairs are activated along one dimension in a manner such that only one source and one detector are operating throughout the array at a given time. After each of the sources and detectors along one dimension are activated, the minimum transmittance point (i.e., the least amount of light passing through the beam) is determined. After determining this minimum transmittance point, the source-detector pairs along the other dimension are sequentially activated in a similar manner. Once again, only one source and one detector are activated at any one time, and a transmittance value for each source-detector pair is determined. Along this other dimension, it is not the minimum transmittance point that the system determines, rather it is the edges of the plume that the system locates. The distance between the edges of the plume represents the length of intersection between the light beam along the other dimension at the minimum transmittance point. The measurement process may be repeated, reversing the roles of the perpendicular arrays to find the minimum transmittance point and the edges of the plume in the other dimension.

Several other advantages are realized using such a two-dimensional smoke opacity measurement system. One such advantage is that the system may optionally determine improper placement of the array, and generate an error signal if any source-detector pairs closest to any of the outer bounds of the array do not yield a transmittance approaching 100%, indicating that the smoke plume is contacting that bound of the array. While it is possible to extend such a system to certain non-circular exhaust plume shapes, if it is so desired to limit the system to circular exhaust plumes, the system may also ensure circularity and non-distortion of the plume by examining the transmittance variances between source-detector pairs along each dimension.

Further objects, features and advantages of the invention will become apparent from a consideration of the following description and the appended claims when taken in connection with the accompanying drawings.

BRIEF DESCRIPTION OF THE DRAWINGS

Figure 1:
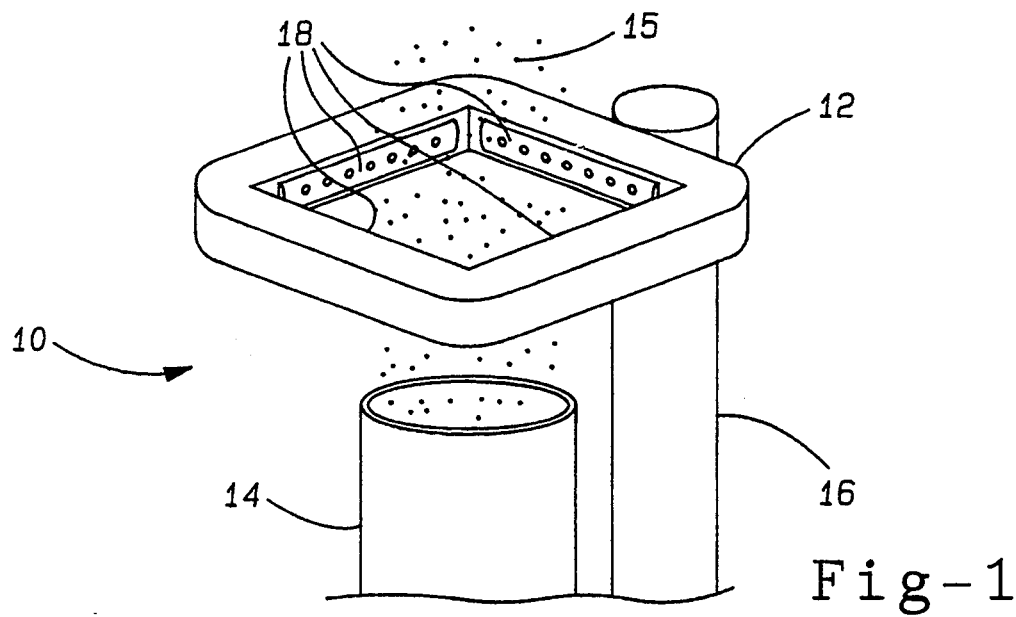
FIG. 1 depicts the apparatus disclosed herein as mounted to a vertical exhaust pipe.

FIG. 1 depicts a typical system configuration of the smoke opacity measurement system 10 including light extinction matrix (LEM) 12 attached to exhaust pipe 14. Exhaust pipe 14 may connect to the exhaust manifold of a diesel engine (not shown) or to a variety of smoke emitting sources. Attached to exhaust pipe 14 is support arm 16 which supports LEM 12 (attachment to exhaust pipe not shown) and extends to maintain LEM 12 above exhaust pipe 14 so that emitted plume of smoke 15 passes within the bounds of LEM 12. To the inner walls 18 of LEM 12 are attached matched sets of light sources and light detectors, to be explained further with respect to FIGS. 2 and 3. LEM 12 defines a plane which is substantially perpendicular to an imaginary longitudinal axis defined by exhaust pipe 14 and plume 15. The sources and detectors mounted to inner walls 18 of LEM 12 are mounted so as to project beams of light substantially parallel to the plane defined by LEM 12.

Figure 2:
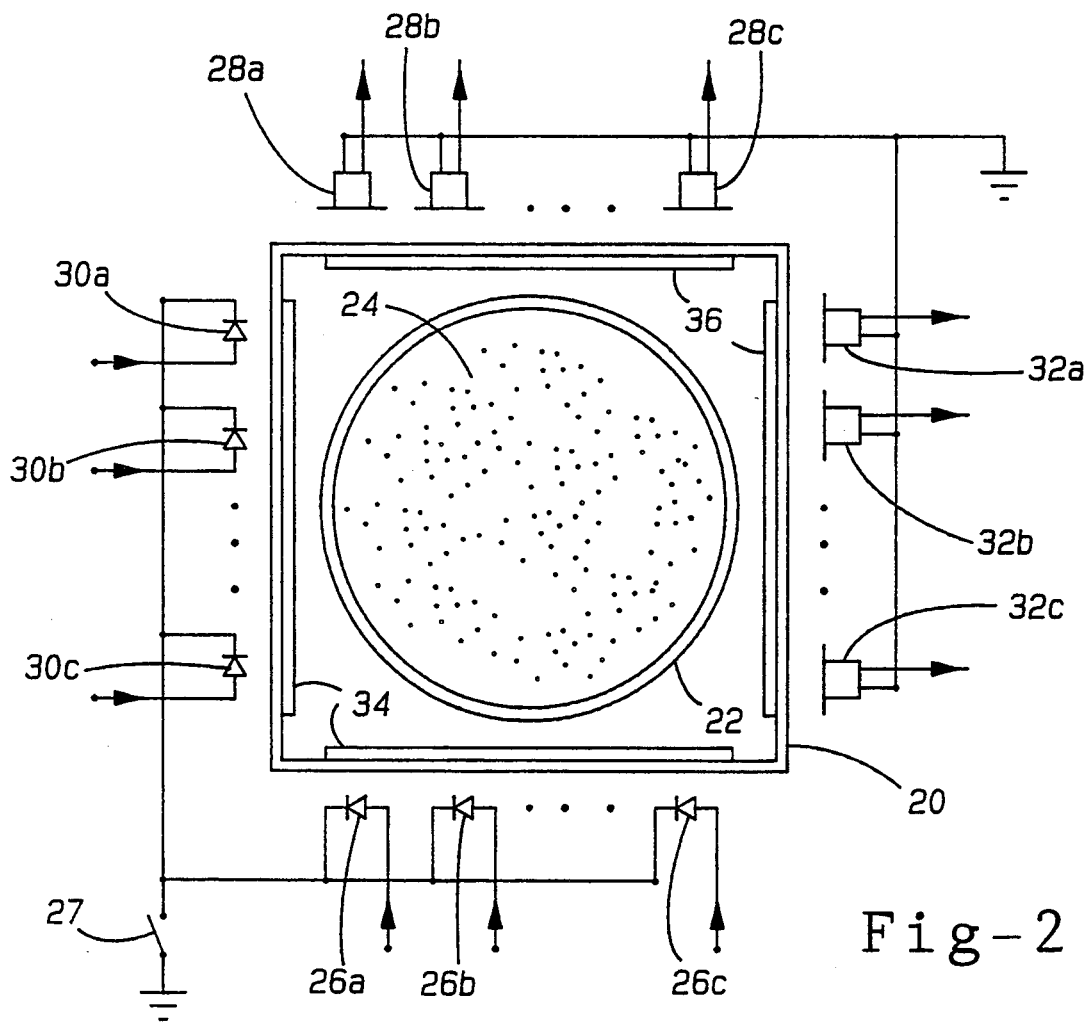
FIG. 2 is a diagram of a top view of a light extinction matrix which shows the matched light source-detector pairs.

FIG. 2 depicts one embodiment of LEM 12 from a top view looking down towards the open end of exhaust pipe 22. Exhaust pipe 22 emits plume of smoke 24 which, in a diesel exhaust system, contains particulate matter whose particle size and density determines the opacity of exhaust plume 24. In this particular embodiment, light sources and detectors surround a rectangular array 20. Light emitting diodes (LED) 26a–c exemplify the light sources and are arranged on one side of rectangular array 20 to oppose light detectors 28a–c. LED's 30a–c are arranged on the other side of array 20 to emit light in a direction towards detectors 32a–c substantially perpendicular to light beams emitted by LED's 26a–c. LED's 26a–c and 30a–c as well as light detectors 28a–c and 32a–c are controlled by inputs and outputs of the circuit depicted in FIG. 3. When a positive electrical signal is applied to the cathode of one of LED's 26a–c or 30a–c and switch 27 is closed, connecting the anode of that LED to ground, that LED emits a beam of light in the direction of the smoke plume. The light travels across array 20 toward the light detectors. One terminal of each of detectors 28a–c and 32a–c is connected to ground while the other terminal leads to the output of the electronic circuit and indicates whether the respective detector has detected light emitted from a given LED. Light emitted from LED's 26a–c and 30a–c passes through lenses 34 which refocus light emitted by the LED's along each dimension for travel in a substantially parallel direction across the array. Similarly, lenses 36 are placed in front of light detectors 28a–c and 32a–c and collect light that has traversed array 20 and focuses that light onto the light detectors.

Referring more specifically to the operation of the LED's and detectors depicted in FIG. 2, an exemplary scheme of activating the LED's and detectors to effectuate smoke opacity measurements will be described below. As an initial point, the opacity of plume 24 depends upon the size and density of the particles contained therein. In areas where the intersection between emitted light and smoke plume 24 is a maximum, there will be a minimum transmittance of light across array 20. Conversely, in areas where the intersection between plume 24 and emitted light is a minimum, there is a maximum transmittance of light across array 20. Therefore, by examining the magnitude of detected light for each source-detector pair, it is possible to construct a profile of plume 24. If such a profile can be generated along both dimensions, it is possible to develop a two-dimensional profile of plume 24 and determine the length of intersection of a light beam at the point of minimum transmittance.

One scheme of light emissions and detections entails sequentially activating the LED's and corresponding detectors along one dimension, then sequentially activating LED's and their corresponding detectors along the other dimension. One sequence of emissions and detections could occur as follows. An electronic controller (not shown) applies an electronic signal to the positive terminal of LED 26a and also closes grounding switch 27 causing LED 26a to emit a beam of light across the array in the direction of light detector 28a. In order to minimize cross talk from adjacent source-detector pairs, the matched source-detector pairs are enabled in a sequential, mutually exclusive order. Thus, LED 26a and detector 28a are activated as a pair, and no other source-detector pair is activated. After source 26a and detector 28a have been activated then deactivated, LED 26b and detector 28b are activated in the same manner as were LED 26a and detector 28a. Similarly, LED 26c and detector 28c are activated following the activation of LED 26b and detector 28b. Detectors 28a-c output a magnitude signal that varies in accordance with the amount of light detected. The sequence is then repeated for LED's 30a-c and detectors 32a-c.

After sequentially activating each source-detector pair along a first dimension, a transmittance value for each source-detector pair will have been determined. The source-detector pair between which a minimum transmittance value is measured defines a diameter of the circular plume, as the light beam must traverse the greatest amount of particulate matter. By examining the variance between transmittance values detected by adjacent light detectors, the shape or profile of plume 24 may be constructed. The diameters along each dimension of the plume of smoke may be measured by determining the source-detector pairs at which the transmittance has risen to approach 100% on both sides of the plume. The distance between like elements of the pairs (e.g., between the detector measuring 100% transmittance on the one side of the plume and the detection measuring 100% transmittance on the other side of the plume) is a measure of the plume diameter. This diameter is the length of intersection at the minimum transmittance value in the perpendicular direction. This value is necessary in calculating the smoke density of plume 24.

The length of intersection at the point of maximum opacity between a beam of light and plume 24 is determinable because LED's 26a-c and 30a-c and detectors 28a-c and 32a-c are positioned around LEM 12 at equally spaced intervals. The resolution of the system depends upon the number of LED's and light detectors per unit length. If an array is 8"×8" and a resolution of a ¼ inch is desired, 32 source-detector pairs must be aligned along each dimension for a total of 64 source-detector pairs. A greater resolution is obtainable by positioning a greater number of LED's and light detectors per unit length along each dimension of the array.

Figure 3:
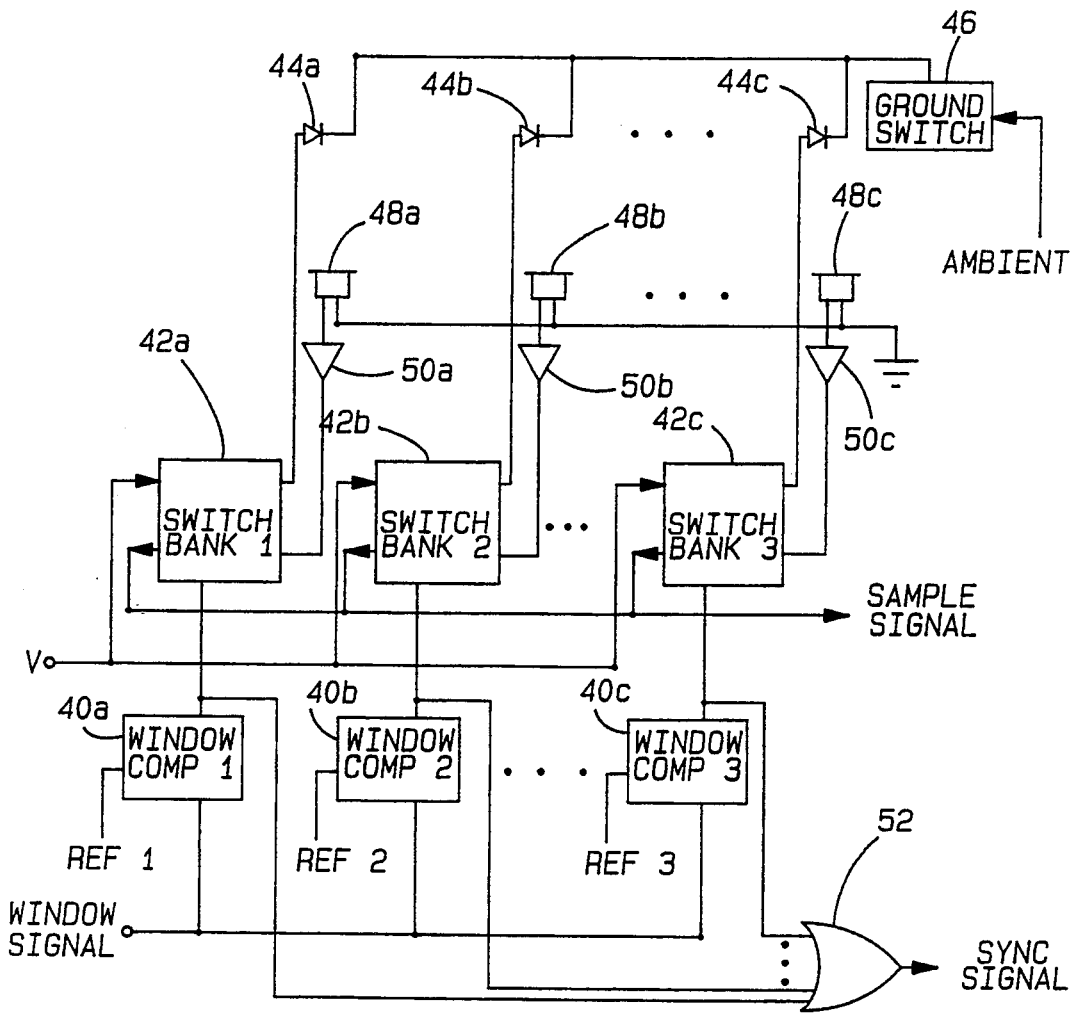
FIG. 3 is a block diagram of an electrical system which may be used to activate the source-detector pairs and generate an output signal therefrom.

FIG. 3 depicts one embodiment of a circuit for activating the LED's and detectors in the manner described with respect to FIG. 2. It should be noted, however, that the circuit described herein is only one circuit which could be used to activate and deactivate the LED's and light detectors. It is a general object of this circuit to illuminate one LED and activate one detector for any given time interval and to sequentially activate each LED and detector over a predetermined detection period. In this particular circuit, the LED's are activated sequentially in accordance with the magnitude of a control signal. In FIG. 3, there are three sets of window comparators 40a-c, switch banks 42a-c, LED's 44a-c, and detectors 42a-c; however, the actual circuitry incorporates as many sets of the above mentioned components as there are LED's aligned around the array. If there are 32 sets of LED's and detectors there will be 32 window comparators, 32 switch banks, 32 LED's, and 32 detectors in the circuit implemented in FIG. 3.

Figure 4:
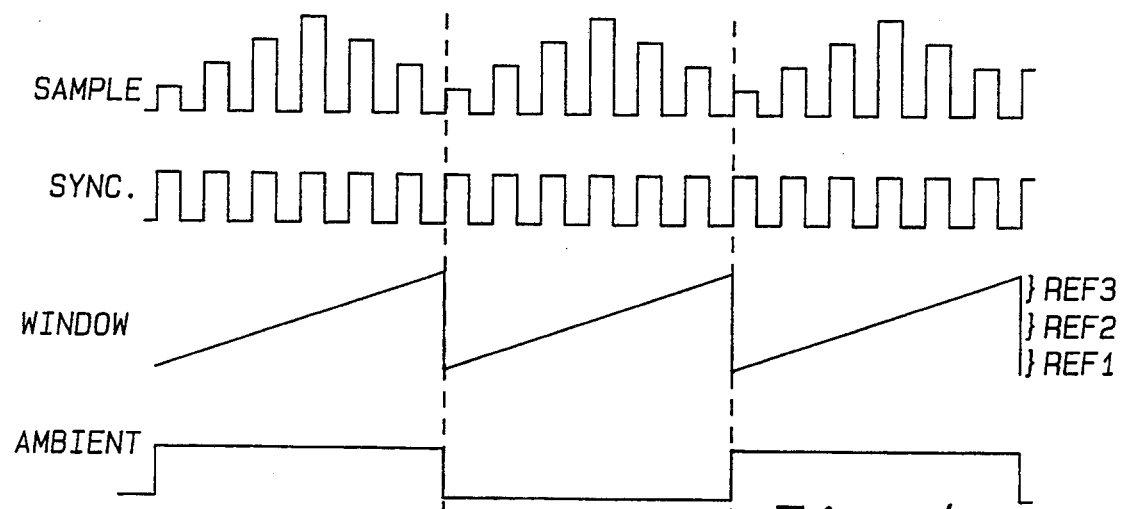
FIG. 4 depicts waveforms which are input into the electrical system depicted in FIG. 3 to activate the light sources and detectors and also depicts the output waveforms generated by the electronic circuit of FIG. 3.

A WINDOW signal is input into window comparators 40a-c, and the outputs of window comparators 40a-c activate the respective switch banks 42a-c. The WINDOW signal input to the circuit of FIG. 3 is a saw toothed waveform depicted in FIG. 4. Window comparator 40a outputs a logic 1 signal when the level of the WINDOW signal is within the bounds as specified by the incoming reference signals REF1, REF2, and REF3, respectively. For example, REF1 may be relatively low voltage which causes window comparator 40a to activate switch 42a when the WINDOW signal is at zero volts until it has risen to the low voltage boundary of window comparator 40b as defined by REF2. As the WINDOW signal saw tooth rises to its peak, each of the window comparators 40a-c will have sequentially activated and deactivated their respective switches 42a-c. FIG. 4 demonstrates the relationship between the ranges of REF1, REF2 and REF3.

When switch bank 42a is activated, a first switch applies a voltage signal V to LED 44a. The activation of LED 44a is dependent upon the application of V and the state ground switch 46 which creates a ground path when closed for LED's 44a-c when ground switch 46 is closed and disables a path to ground when ground switch 46 is open. The waveform for the signal to open and close ground switch 46 is represented by the AMBIENT signal shown in FIG. 4. This signal has a period twice that of the WINDOW signal so that during a first period LED's 44a-c are activated as are detectors 48a-c, while during a second period of the WINDOW signal, LED's 44a-c are not activated yet detectors 48a-c are activated. The AMBIENT signal thus enables activation of LED's 44a-c during every other WINDOW period. When LED's 44a-c are not activated and the detectors 48a-c are activated, ambient light is detected. The ambient light detected by each detector is filtered out by the controller from light detected by the same detector during the previous detection period during which the LED's were activated.

The output signals of detectors 48a-c are conditioned by buffers 50a-c, respectively, then pass through a second switch of switch banks 42a-c which output the SAMPLE signal that connects to a control unit or microprocessor. Additionally, window comparators 40a-c connect to OR gate 52 which generates a SYNC signal. The SYNC signal is depicted in FIG. 4 and defines the intervals during which examination of the SAMPLE signal should occur. The SYNC signal is used in conjunction with the SAMPLE signal to define the intervals during which the magnitude of the OUTPUT signal is examined.

FIG. 4 depicts both the input and the output signals associated with the circuit of FIG. 3. The AMBIENT signal and the WINDOW signal are input into FIG. 3. As described above, the AMBIENT signal has a period twice that of the WINDOW signal. When the AMBIENT signal is high, the SAMPLE signal reflects the magnitude of the light detected by detectors 48a-c of FIG. 4 while LED's 44a-c are activated, respectively. When the AMBIENT signal is low, the SAMPLE signal reflects the magnitude of the ambient light collected by detectors 48a-c while the LED's are not activated. Furthermore, the output signal SYNC signal is used to more accurately differentiate the SAMPLE pulses on the output bus. When the SYNC signal is high, the SAMPLE signal from the output bus is examined to determine its magnitude.

Figure 5:
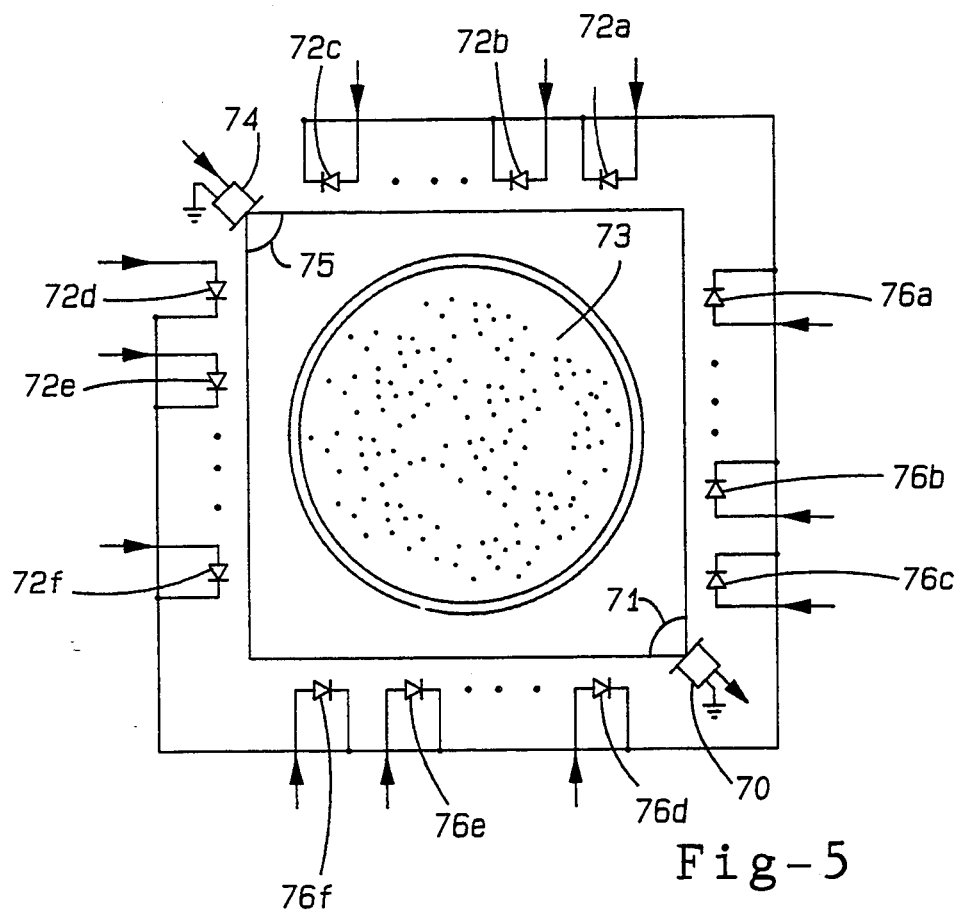
FIG. 5 depicts a second embodiment of the light extinction matrix using a reduced number of light detectors and an increased number of light sources.

FIG. 5 depicts an alternate embodiment of LEM 12. In this embodiment, detectors 70 and 74 are positioned in corners of a substantially rectangular LEM 12. LED's 72a-f are sequentially activated to project beams of light in the direction of plume 73 while detector 70 is also activated. Detector 70 collects light from the sequentially activated LED's 72a-f as the light passes through focusing lens 71. In In this manner one LED is not paired with one detector; rather, a set of LED's corresponds to one detector. Similarly, detector 74 is located in a corner opposite detector 70. While detector 74 is activated, light emitting diodes 76a-f are sequentially activated to project beams of light which pass through focusing lens 75 and are detected by detector 74. The number of light detectors may be thus reduced greatly while the number of LED's is increased. Because of position of detectors 70 and 74 and LED's 72a-f and 76a-f along the array is known, a profile of a plume of smoke may be generated based on the magnitude of the opacity detected by each detector for each corresponding LED. Using simple geometric calculations, the profile of plume of smoke 73 may be determined as may its diameter. The circuit to activate the LED's and detectors in the embodiment depicted in FIG. 5 will be modified so that light detector 70 is activated upon activation of any of LED's 72a-c, and light detector 74 is activated upon activation of any of LED's 76a-f. Similarly, as described with reference to FIG. 2, the resolution of the system is varied according to the number of LED's per unit length placed along the array.

Figure 6:
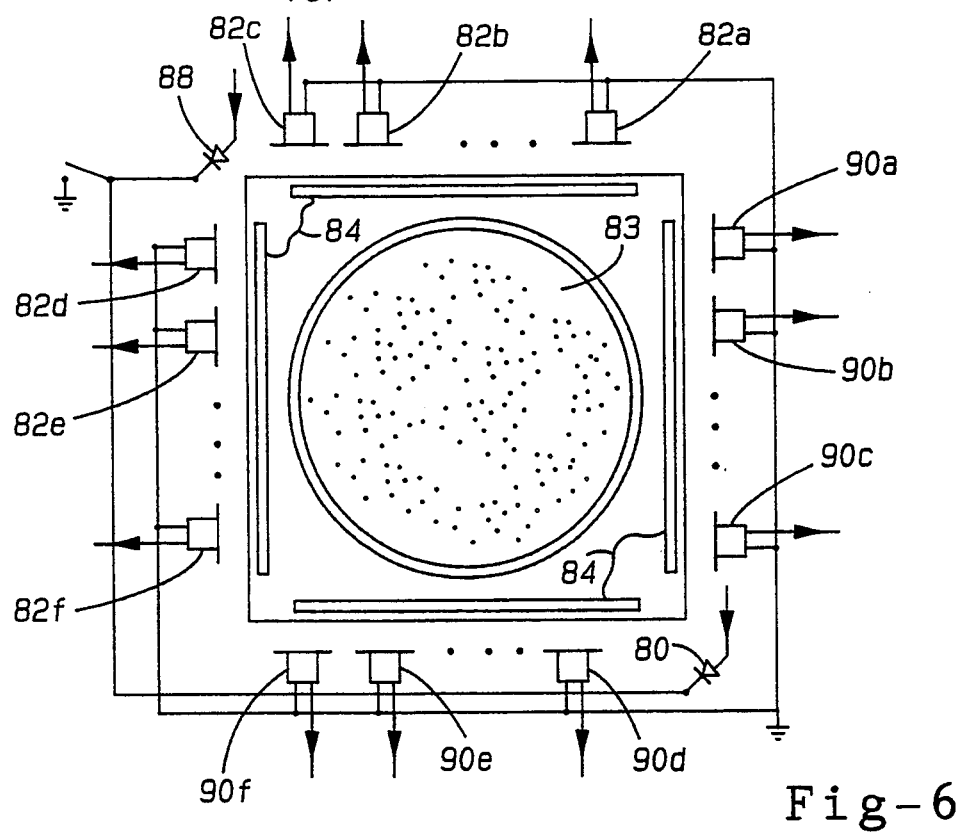
FIG. 6 depicts a third embodiment of the light extinction matrix implemented using a reduced number of light sources and an increased number of light detectors.

FIG. 6 depicts a third embodiment of LEM 12. In this embodiment LED's 80 and 88 are located at the corners of the array and light detectors 82a-f and 90a-f are located along the sides of the array. When LED 80 is activated, light detectors 82a-f are sequentially activated to determine the magnitude of the light traveling through smoke plume 83. Focusing lenses 84 are positioned in front of each set of detectors to focus the light onto the corresponding detectors. LED 88 is located in a corner opposite LED 80, and when activated, light detectors 90a-f are sequentially activated to detect the transmittance of the light passing between the LED and detector. As in the second embodiment of this invention, simple geometric calculations may be performed to determine the diameter of the plume 83. Also, the electronic system depicted in FIG. 3 would require modifications such that while either of LED's 80 or 88 are activated, light detectors 82a-f and 90a-c are sequentially activated, respectively, to detect light as it passes through a plume of smoke 83.

It is to be understood that the invention is not limited to the exact construction illustrated and described above, but that various changes and modifications may be made without departing from the spirit and scope of the invention as defined in the following claims.

I claim:

1. Apparatus for measuring the opacity of an exhaust plume of smoke having an imaginary longitudinal axis, said apparatus comprising:

an array of light sources and light detectors arranged in a plane that is substantially perpendicular to said axis, said light sources and detectors being arranged so as to define a plurality of light paths which are displaced about and traverse the planar area bounded by said array and further defining two sets of a plurality of matched source-detector pairs providing mutually perpendicular light paths;

means for activating said sources and said detectors to define source-detector pairs so that light emitted by said sources is absorbed by said detectors; and means operatively associated with said detectors for determining the magnitude of the transmittance of light through said exhaust plume where said plume and emitted light intersect, where said emitted light is of a predetermined intensity and light absorbed by a corresponding detector of a given source-detector pair defines the transmittance of the exhaust plume at said intersection.

2. The apparatus of claim 1, wherein said two sets of a plurality of matched source-detector pairs further comprise a first set of matched source-detector pairs where each source and detector substantially oppose each other and define light paths in a first direction, and a second set of matched source-detector pairs where each source and detector substantially oppose each other and define light paths in a second direction substantially perpendicular to said first direction.

3. The apparatus of claim 1, wherein said light emitting array comprises an equal number of matched source-detector pairs in both said first and second sets.

4. The apparatus of claim 3 for determining the opacity of an exhaust plume of smoke where said plume is emitted from a substantially circular exhaust pipe, further comprising:

means for determining a minimum transmittance path through said circular exhaust plume along one of said light paths where said minimum transmittance defines a maximum opacity for said circular exhaust plume to locate a diameter of said circular exhaust plume;

means for determining a first transmittance path proximately located near a first edge of said circular exhaust plume along a light path substantially perpendicular to said minimum transmittance path where said first transmittance path defines a first tangent to said circular exhaust plume;

means for determining a second transmittance path proximately located near a second edge of said circular exhaust plume along a path substantially parallel to said first transmittance path where said circular exhaust plume is interposed between said first and second transmittance paths and said second transmittance path defines a second tangent to said circular exhaust plume;

means for calculating a separation distance between said first and second transmittance paths to define a length of intersection between the circular exhaust plume and emitted light at said minimum transmittance point; and means for calculating the smoke density of said circular exhaust plume based on said intersection length and said minimum transmittance.

5. The apparatus of claim 2, further comprising a support means defining a generally square frame defining mutually perpendicular legs and wherein said array comprises a first source supported at a first intersection of two of said legs and a first set of detectors supported by two of said legs opposing said first intersection, and said first set of detectors are sequentially activated while the first source is activated, and a second source supported at a second intersection of said legs opposite said first intersection and a second set of detectors supported by two of said legs opposing said second intersection and said second set of detectors are sequentially activated while the second source is activated, and said first and second sources are sequentially operated.

6. The apparatus of claim 2, further comprising a support means defining a generally square frame defining mutually perpendicular legs and wherein said array comprises a first detector supported at a first intersection of two of said legs and a first set of sources supported by two of said legs opposing said first intersection, and said first set of sources are sequentially activated while said first detector is activated, and a second detector supported at a second intersection of said legs opposite said first intersection and a second set of sources supported by two of said legs opposing said second intersection, and said second set of sources are sequentially activated while said second detector is activated, and said first and second detectors are sequentially operated.

7. The apparatus of claim 1 wherein said apparatus is affixed to an exhaust pipe of a diesel engine.

8. The apparatus of claim 1, wherein said means for measuring the opacity of an exhaust plume further comprises:

support means for said array;

at least one of said source-detector pairs which define one of said light paths in close proximity to said support means in order to detect a substantially high transmittance, indicating an absence of smoke in close proximity to said support means; and signal means activated upon detection of smoke in close proximity to said support members.

9. Method for measuring the opacity of an exhaust plume of smoke having an imaginary longitudinal axis, said method comprising the steps of:

directing an array of light beams through said plume in a plane that is substantially perpendicular to said axis, detecting variations in the intensity of the light from said beams emerging from said plume using detectors, where a first set of a plurality of substantially parallel beams is directed along one path and a second set of a plurality of substantially parallel light beams is directed along a path substantially perpendicular to said first set of light beams;

determining variations in the magnitude of the transmittance of light from individual beams through said exhaust plume with said detectors where said plume and emitted light intersect, where said emitted light is of a predetermined intensity and the magnitude of the detected light is in accordance with the opacity of said plume.

10. The method defined by claim 9, wherein the step of directing an array of light beams comprises directing an equal number of light beams along each perpendicular path.

11. The method as defined by claim 10 for determining the density of an exhaust plume of smoke where said plume is emitted from a substantially circular exhaust pipe, further comprising the steps of:

constructing a profile of said plume using the transmittance variances for adjacent detectors along each path of source-detector pairs;

examining said transmittance profile for a relatively consistent increase in opacity between adjacent detectors to a maximum value, then for a relatively consistent decrease in opacity between adjacent detectors to substantially zero opacity in order to determine the circularity of said plume;

determining a first diameter of said circular plume in a direction substantially perpendicular to said one set of light beams as defined by a separation distance between two source-detector pairs at which the measured opacity of said plume tapers substantially to zero;

determining a second diameter of said circular plume in a direction substantially perpendicular to said other set of light beams as defined by a separation distance between two source-detector pairs at which opacity of the plume tapers substantially to zero;

comparing said first and second diameters to insure that said diameters are within a predetermined range of each other; and calculating a smoke density value as a function of the maximum opacity value and the diameter of said plume in a substantially perpendicular direction to that of the light beam rendering said maximum opacity value.

12. The method as defined by claim 9, wherein the step of directing an array of light beams comprises:

activating a first light source located at a first corner of a substantially rectangular array;

sequentially activating a first set of light detectors arranged so as to oppose said first light source while said first light source is activated;

activating a second light source after activating said first light source located at an opposite corner of said first corner;

sequentially activating a second light set of light detectors arranged so as to oppose said second light source while said second light source is activated.

13. The method of claim 9, wherein the step of directing an array of light beams is carried out with a substantially rectangular array comprising a first detector supported at an intersection of two support means and a first set of sources supported by another two support means where said support means lie in the plane of said light beams, and said first set of sources are sequentially activated while said first detector is activated, and a second detector supported at an intersection of said other two support means and a second set of sources supported by said first two support means, and said second set of sources are sequentially activated while said second detector is activated, and said first and second detectors are sequentially operated.

14. The method defined by claim 9 wherein the step of directing an array of light beams further comprises directing said light beams across an exhaust plume of a diesel engine.

15. The method defined by claim 9, wherein the step of measuring the opacity of an exhaust plume further comprises the steps of:

determining if a path of substantial transmittance exists along detection paths in close proximity to outermost boundaries of said plane, indicating an absence of smoke in close proximity to said outer boundary;

determining if at least one source-detector pair not in close proximity to said outer boundary has a substantially low transmittance to indicate the presence of smoke within said array;

signaling upon detection of smoke in close proximity to said support members if such a condition is determined, indicating proper placement of said array to said exhaust plume.

16. Apparatus for measuring the opacity of an exhaust plume of smoke having an imaginary longitudinal axis, said apparatus comprising:

an array of light sources and light detectors arranged in a plane that is substantially perpendicular to said axis, said light sources and detectors being arranged in a substantially rectangular manner so as to define a plurality of light paths which are displaced about and traverse the planar area bounded by said array;

two sets of a plurality of matched source-detector pairs disposed on said rectangular array that define mutually perpendicular light paths, including a first set of matched source-detector pairs where each source and detector substantially oppose each other and define light paths in a first direction and a second set of matched source-detector pairs where each source and detector substantially oppose each other and define light paths in a second direction substantially perpendicular to said first direction;

means for activating said sources and said detectors so that light emitted by said sources is absorbed by said detectors;

means operatively associated with said detectors for determining the magnitude of the transmittance of light through said exhaust plume where said plume and emitted light intersect, and said emitted light is of a predetermined intensity and light absorbed by a corresponding detector of a given source-detector pair defines the transmittance of the exhaust plume at said intersection;

means for determining a minimum transmittance path through said exhaust plume along one of said light paths where said minimum transmittance defines a maximum opacity for said exhaust plume to locate a diameter of said plume;

means for determining a first transmittance path proximately located near a first edge of said plume along a light path substantially perpendicular to said minimum transmittance path where said first transmittance path defines a first edge of said exhaust plume;

means for determining a second transmittance path proximately located near a second edge of said plume along a path substantially parallel to said first transmittance path where said exhaust plume is substantially interposed between said first and second transmittance paths and said second transmittance path defines a second edge of said exhaust plume;

means for calculating a separation distance between said first and second transmittance paths to define a length of intersection between the exhaust plume and emitted light at said minimum transmittance point;

means for calculating the smoke density of said exhaust plume based on said intersection length and said minimum transmittance;

support means for said array;

at least one of said source-detector pairs which define one of said light paths in close proximity to said support means in order to detect a substantially high transmittance, indicating an absence of smoke in close proximity to said support means; and signal means activated upon detection of smoke in close proximity to said support members.

* * * * *